United States Patent [19]

Sasmor et al.

[11] 4,364,929

[45] Dec. 21, 1982

[54] GERMICIDAL COLLOIDAL LUBRICATING GELS AND METHOD OF PRODUCING THE SAME

[75] Inventors: Ernest J. Sasmor, Yonkers, N.Y.; Kenneth G. Rothwell, Easton, Conn.

[73] Assignee: The Purdue Frederick Company, New York, N.Y.

[21] Appl. No.: 145,232

[22] Filed: Apr. 30, 1980

Related U.S. Application Data

[63] Continuation of Ser. No. 26,401, Apr. 2, 1979, abandoned, which is a continuation of Ser. No. 949,378, Oct. 6, 1978, abandoned.

[51] Int. Cl.³ .................. A61K 31/79; A61K 33/18; A61K 31/74; H01B 1/06
[52] U.S. Cl. .................................. 424/80; 252/518; 424/78; 424/150
[58] Field of Search .................. 424/78, 80, 150; 252/518; 128/518

[56] References Cited

U.S. PATENT DOCUMENTS

| | | | |
|---|---|---|---|
| 2,550,622 | 4/1951 | Taub | 424/150 |
| 2,567,584 | 9/1951 | Thomas | 424/150 |
| 2,726,982 | 12/1955 | Ocks et al. | 424/78 |
| 3,214,384 | 10/1965 | Wilson | 424/150 |
| 3,671,545 | 6/1972 | Halpern | 424/80 |
| 3,876,771 | 4/1975 | Denner | 424/80 |
| 3,886,268 | 5/1975 | Halpern | 424/80 |
| 3,927,205 | 12/1975 | Ohno et al. | 424/361 |
| 4,010,259 | 3/1977 | Johansson | 424/150 |

*Primary Examiner*—Douglas W. Robinson
*Attorney, Agent, or Firm*—Steinberg & Raskin

[57] ABSTRACT

Germicidal properties are provided for colloidal lubricating gels without destruction of the physical properties of the colloidal gel by the incorporation therein of an iodophor within strict limits as to the quantities and relative quantities of the iodophor-former, the iodine and the gel-forming colloid. These germicidal colloidal lubricating gels remain stable and retain their germicidal effectiveness. As a result, these compositions can be used for the lubrication of catheters and other instruments to facilitate their insertion into a body cavity and because these compositions do not cause pain or irritation their use reduces the risk of infection and tissue-trauma.

4 Claims, No Drawings

GERMICIDAL COLLOIDAL LUBRICATING GELS AND METHOD OF PRODUCING THE SAME

This is a continuation, of application Ser. No. 026,401, filed Apr. 2, 1979 now abandoned this which is a continuation of Ser. No. 949,378 filed Oct. 6, 1978 now abandoned.

BACKGROUND OF THE INVENTION

The use of lubricating gels to reduce frictional irritation and pain associated with the insertion of catheters and instruments is well known. When catheters, and in particular the indwelling catheter, or when instruments are introduced into a body cavity, a certain measure of tissue-trauma, pain and irritation results, but this is generally without clinical sequelae for most body cavities. A particular problem arises however, when such catheters and instruments are used to explore certain body cavities known to harbor, or to be exposed to pathogenic organisms as for example, the genito-urinary tract, particularly when such procedures requires the retention of the catheter or when multiple instrumentation is necessary in that microbial infection virtually always occurs.

The presence of pathogenic organisms, as well as other microbes residing in the male and female urethra is well documented and infections of the bladder and urinary tract occur at an inordinately high incidence despite the institution of rigorous aseptic operatively techniques and excellent nursing care, as well as in the presence of the administration of antibiotics and other germicides. New infections occur each time when microbial organisms from outside gain access to the bladder through the urethra. The pathogens most often involved are those resident in the patient's environment and these have been found to be identical to those isolated from the vagina, pudendum, anus and urethra of the individual, thus establishing an instrumental conduit action to be a contributory cause.

The normal tissue defense mechanisms usually prevent clinical infection by microbial invaders in the urethra and washout effect of urinary flow while voiding, together with the intrinsic antibacterial properties of the urethral and vesical mucosal enzymes, ordinarily eliminates the organisms before these become a thread to the individual. These normal defense mechanisms however, become inadequate under certain clinical situations such as, (1) trauma to the urethral meatus and urethra to result in a fertile medium for bacterial growth and for impairment of the antibacterial activity of the urothelium, (2) an overwhelming inocculum of bacteria delivered to the urethra over a period of time against which the defense mechanism are inadequate, such as fecal contamination of an indwelling catheter, (3) relatively obscure changes in the length or caliber of the urethra and atrophic changes in the urethral mucosa, and, (4) after repeated catheterization and instrumental exploration of the genito-urinary tract or when indwelling catheters are utilized, and genito-urinary infection almost always occurs.

This extremely high incidence of urethral and bladder infection after catheterization and/or instrumentation procedures has been directly attributed to tissue injury from the procedure, as well as a result of the microbial conduit effect provided by the catheter and/or instrument. The urethra has a high microbial population which reside mainly in the distil portion of the urethra, but as the proximal urethra is ascended, the microbial population decreases to the point where there are virtually no pathogens and/or microbes in the proximal urethra where it emerges from the bladder. The tissues of the bladder and proximal urethra are known to be essentially germ-free. The proliferation of infection following such instrumentation had been unexplained for years until it was shown that the natural body defenses and natural antimicrobial bodies are temporarily destroyed in the course of tissue-trauma associated with such instrumental exploratory procedures and infection soon followed. Thus, when airborne organism, together with resident microbes of the surrounding anogenital area are carried along the urethra by the penetrating device, the temporary absence of the natural antimicrobial tissue defenses, as a result of operative tissue-trauma, no longer accted to destroy these invaders and infection almost always occurred.

In the effort to reduce or eliminate this source of infection, various local-acting antiseptic and/or antibiotic preparations were utilized. The use of phenol ointments were tried, but soon rejected when problems of discomfort, pain and irritation occurred. The antibiotic lubricating gel approach also failed since the topically-active polymixin-benzalkonium antibiotic ointment products have a limited and incomplete antimicrobial spectrum giving rise to resistant strains of micro-organisms and placed the patent in new jeopardy.

It has long been established that iodine is perhaps the most effective and desirable topical antimicrobial agent and its pharmaceutical preparations enjoy wide-spread usage in clinical medicine, first-aid procedures and environmental antisepsis. Despite the wide use of iodine as a topical germicide, lubricating gel compositions intended for use with catheters and instruments, do not include iodine as the antimicrobial agent because of the well known, inherent limitations of iodine. Iodine is a strong corrosive, oxidizing agent possessing a high order of chemical reactivity which tends to interact with most catheters and instruments, as well as to destroy the stability of most pharmaceutical compositions, and in particular, colloidal lubricating gels. Furthermore, the high vapor pressure of iodine precludes its use in tight compartments, such as the urethra and body cavities such as the bladder. These inherent limitations, together with the known high acute toxicity and local irritation of iodine has limited its use in topical antiseptic preparations to virtually only the aqueous and/or alcoholic solution.

When the use of iodine as the germicidal agent in a colloidal lubricating gel is considered, further complications arise. The strong electrical properties of iodine rapidly modifies the colloidal properties of the gel to result in coagulation of the colloid, rendering such gels useless. Apart from the destructive physical/chemical role of iodine in neutralizing the electronic balance of the colloidal system, iodine cannot be used in a gel coming into contact with nitrogen-amino substances as would be present in the urine coating the urethra when the germicidal lubricating gel is used with catheters inserted into the genito-urinary tract, since iodine reacts with such amino compounds to produce chemical compounds of great hazard to humans.

The development of iodophor germicidal compounds constituted a marked advance in overcoming the general inherent biologic limitations of elemental iodine since this new class of compounds by virtue of their unique chemical and physical structure modified the physiologic behavior of iodine without changing its broad spectrum germicidal properties. An iodophor involves the formation of a chemical complex between an organic polymeric iodine carrier, as for example, polyvinylpyrrolidone, nonylphenoxypoly-(ethyleneoxy)ethanol, and other detergent organic polymer compounds, with elemental iodine so that the resultant formed iodophor complex possesses new and novel properties which differ from its component moieties.

The bond between the organic carrier and the elemental iodine is essentially ionic and there is a shift in the ultraviolet absorption spectrum of iodine as well as an increased aqueous solubility for iodine. Thus, while elemental iodine is soluble to the extent of 0.034 percent in water at 25° C., it is soluble to the extent of 0.58 percent in a one percent aqueous solution of polyvinylpyrrolidone-iodine through the iodopher formation to result in polyvinylpyrrolidone-iodine. This 17-fold increase in the solubility of iodine by complexing with polyvinylpyrrolidone to form an iodophor compound enables the use of iodine as a safe and effective germicide in aqueous solution. This bond between polyvinylpyrrolidine and iodine is ionic in character and the iodine cannot be extracted using the usual iodine extracting solvents, i.e. carbontetrachloride, and also the vapor pressure of iodine is reduced essentially to zero.

Further proof of the modification of the noxious biologic properties of elemental iodine, through iodophor formations, is seen in the marked reduction in irritation and toxicity for the formed complex, when compared to that of elemental iodine. Polyvinylpyrrolidone-iodine has an $LD_{50}$ of 1300 mg/kg whereas elemental iodine in water has an $LD_{50}$ of 400 mg/kg. When the gross pathology is studied for two groups of treated animals with aqueous iodine solution and polyvinylpyrrolidone-iodine solution, those treated with polyvinylpyrrolidone-iodine showed no hemorrhage or other gross pathology, whereas all animals treated with the aqueous iodine solution exhibited hemorrhagic gastritis. Tests for ittitation on intact skin, damaged skin and the eyes, establish polyvinylpyrrolidone-iodine to be singularly free of noxious irritation whereas the conventional aqueous solution of iodine was markedly irritated.

Studies by in-vivo and in-vitro testing for microbicidal efficacy of polyvinylpyrrolidone-iodine established this agent to possess the full microbicidal spectrum of elemental iodine against micro-organisms. A similar chemical and therapeutic biologic profile was established for the iodophor complexes formed between a surface-active iodophor agent, as for example, nonylphenoxy-poly-(ethyleneoxy)-ethanol iodine and other surface-active iodophors, as for example, poly-(oxypropylene)-poly-(oxyethylene) copolymers which are known as Poloxamer-iodine complexes also demonstrate quantitative but not qualitative differences in the modification of physical and chemical properties of iodine although the microbiologic germicidal properties of iodine remained intact.

Pharmaceutical compositions for use as lubricating gels are prepared with certain carbohydrate polymer substances, as for example, cellulose derivatives such as methylcellulose, hydroxyalkylcellulose and carboxymethylcellulose, or vegetable gums, such as alginic acid, esters of alginic acid, tragacanth, and gum karaya, or mixtures of these to form aqueous colloidal dispersions in the form of a viscous gel. Such colloidal gels are applied to the surface of catheters and instruments prior to their insertion into a body cavity to provide lubricating slip and therefore must be compatible with the catheter or instrument.

SUMMARY OF THE INVENTION

Generally speaking, in accordance with the invention, a germicial colloidal lubricating gel for use on and in the body is provided comprising a physiologically compatible colloidal gel-forming polymer, water and an iodophor or a substance capable of forming an iodophor with iodine and iodine, the substance capable of forming the iodophor being present in an amount of 0.3–4 parts by weight for all such substances other than povidone and in an amount of 0.5–2 parts by weight in the case of povidone, per each part of the colloidal gel-forming polymer, the colloidal gel-forming polymer being present in an amount of about 0.5–7.5% by weight, the amount of the substance capable of forming the iodophor being present in an amount of 8–12 parts by weight per each part by weight of iodine and the amount of iodine being present in an amount of 0.05–2% by weight of the total.

It is a primary object of the present invention to provide new lubricating germicidal colloidal gels which are particularly suitable for use on catheters and other instruments to facilitate their insertion into a body cavity by providing lubricating slip to reduce frictional resistance and tissue injury while at the same time providing a broad spectrum germicidal action to prevent post-treatment in section.

It is another object of the present invention to provide new germicidal lubricating gel compositions which comprise the colloidal gel-forming substance, particularly cellulose-gelling agents and iodine in an aqueous carrier in the form of a reproducible, homogeneous, stable colloidal gel for use in the lubrication of catheters and instruments to provide an aseptic, essentially germ-free environment in order to reduce the risk of infection as well as tissue-trauma, pain and irritation from use of the instrument.

It is still another object of the present invention to provide stable colloidal lubricating gels with broad spectrum germicidal action as a result of the presence of iodine while avoiding destruction of the gel by the iodine and reduction in the germicidal action of the iodine from the colloidal gel-forming substance.

Other objects and advantages of the present invention will be apparent from a further reading of the specification and of the appended claims.

It is known that iodine reacts with gel-forming polyers, particularly the carbohydrate polymers which are most preferred for colloidal lubricating gels which are used on catheters and other instruments, to modify both the chemical and physical properties of the carbohydrate polymer in such manner as to destroy the chemical, physical and biologic properties of the iodine. Furthermore, ordinarily when a solution of an iodophor is brought into contact with a carbohydrate gel-forming polymer, such as starch or cellulose as well as vegetable gums, decolorization of the iodophor solution takes place with destruction of the iodine. This of course would be expected from a knowledge of the chemistry of iodophor compounds established from the oxidizing properties of iodine are not modified through iodophor formation. When a carbohydrate polymer is added to an iodophor solution, the carbohydrate polymer undergoes general decomposition so that its physical properties are destroyed.

It was found that when iodine is added to aqueous colloid solutions of long-chain carbohydrate polymers, as for example, starch, gums such as karaya, and algin, and cellulose polymer derivatives, that virtually no iodophor formation occurs as is known for other polymers. Thus, when one part of elemental iodine was added to a colloidal solution of carboxymethylcellulose, coagulation of the colloid occurred. Upon washing the precipitate cellulose product with carbon tetrachloride, small amounts of iodine were removed and the washed cellulose precipitate substance regenerated its colloidal properties although to a lesser degree. When other cellulose derivatives, such as hydroxy-propylmethylcellulose was used, again no iodophor formation was observed and the colloidal properties of the cellulose agent was destroyed. Similar failure was observed when elemental iodine was added to starch-colloid gels or to gum karaya and alginic acid colloid gels.

It was unexpectedly found that when iodine is added to a colloidal solution of a gel-forming colloid such as a carbohydrate polymer in the presence of a substrate capable of forming an iodophor, such as povidone, in a ratio of from 8 parts by weight to 12 parts by weight of povidone for each part of iodine added, that a stabilizing effect is observed which prevents the destruction of the colloidal properties of the carbohydrate polymer iodine. It was furtherfound that the addition of povidone may be made either at the same time, or before the addition of iodine to cause the stabilization of the iodine-carbohydrate polymer colloidal dispersion and that iodine concentration within the range of from 0.05–2% by weight of iodine could be incorporated into the colloidal dispersion and the mixture preserved.

It was further determined that the formed iodophor, e.g. povidone-iodine, also possesses a stabilizing property for an iodine-carbohydrate polymer combination when the ratio of the povidone (polyvinylpyrrolidone) is present in the amount of from 0.5 parts by weight to 2.0 parts by weight of povidone for each part of carbohydrate polymer. It was determined that competitive bonding for the iodine occurs between the povidone and the carbohydrate polymer substance, as for example, vegetable gums and cellulose derivatives, which acts to neutralize the colloid coagulative properties of iodine on the carbohydrate polymer colloid, so that stable, homogenous, reproducible colloidal suspensions are preserved.

When the amount of polyvinylpyrrolidone is less than 0.5 parts by weight for each part of carbohydrate polymer is dispersion, then the colloidal properties of the carbohydrate polymer are destroyed by the iodine and coagulation occurs. The solution soon decolorizes indicating a destruction of its iodine content. When the amount of polyvinylpyrrolidone is present in such amount that the concentration of povidone is in excess of the ratio of two parts by weight each part by weight of carbohydrate polymer in colloidal dispersion, stratification of the mixture occurs with separation into two distinct layers. This phase separation destroys the lubricating properties of the composition.

When the iodine concentration of the composition falls below 0.05 percent and the amount of povidone in the solution is less than 0.5 parts by weight for each part of carbohydrate polymer present, the composition rapidly decolorizes with apparent shift in pH to indicate the formation of hydriodic acid. When the amount of titratable iodine exceeds 0.2 percent, coagulation occurs.

From studies conducted of the mechanism of such colloid stabilization, it was postulated that a dynamic equilibrium is established between the complexed iodine and each of the polymeric substances present, that is, povidone and the carbohydrate polymer, which acts to neutralize the coagulent effect of iodine or the colloidal dispersion of the carbohydrate polymer. This coagulent effect arises from the strong negative electric potential of iodine which is in part, neutralized by electrically-charged colloid particles of both the povidone and the carbohydrate; the electrical bonding potential of povidone for iodine being markedly stronger than the electrical bonding potential of the carbohydrate polymer for iodine.

When the povidone moiety complexes with iodine, the electrical balance of the system is now in favor of maintaining the preferred electrical charge on the colloidal suspension to preserve the viscous gel properties of the composition. When the iodine is released, it acts to neutralize these charged colloid particles by reversable complexing to dynamically coagulate the colloid and to release iodine which is available for complexing by the povidone, once again. By the use of a critical balance between the ratio of iodine carrier polymer, povidone, and carbohydrate colloid polymer to control the bound and available iodine levels, a dynamic equilibrium is established which provides the means for stabilizing a colloidal dispersion of a carbohydrate polymer in the presence of iodine which is essential to the formation of germicidal lubricating gel. In this manner the manufacture of a novel, germicidal lubricating gel for use with catheters and instruments, intended for insertion into a body cavity, including the genito-urinary tract, may be accomplished for the first time.

A similar mechanism was determined to exist for other iodine carriers of the generic class of iodophors, as for example, the surfactant iodophor group such as nonylphenoxypoly-(ethyleneoxy)ethanol and the iodophor substance, ioloxamers, a generic name, which are polyoxypropylenepoly-(oxy-propylene)poly-oxyethylene copolymers, so that a stable colloid lubricating gel may be prepared with iodine when essentially the same ratios of ingredients are utiized, that is, not less than 0.3 parts by weight of a surfactant iodophor compound, for each part of carbohydrate polymer used to prepare the gel.

It was further found that the addition of the iodophor and iodine was best accomplished as a polar solution and added to a colloid dispersion of the carbohydrate polymer in polar solvent. When iodine is used with an iodophor polymer substance, it should be previously dissolved in the solution of the iodophor substance before being added to the colloid dispersion. Moreover, all iodine-containing solutions are to be added to the carbohydrate polymer collid solution so that an excess of carbohydrate polyer colloid to iodine is present at all times.

When it is desired to prepare a germicidal lubricating gel, an aqueous solution of the appropriate quantity of the selected iodophor compound or of povidone or a surfactant polymer, capable of forming an iodophor, and iodine is prepared in such concentration as is sufficient to provide not less than 0.5 parts by weight and not more than 2.0 parts by weight of polyvinylpyrrolidone, or not less than 0.3 parts by weight and not more than 4 parts by weight of the surfactant iodophor-former, for each part of carbohydrate polymeric substance selected to form the colloidal gel dispersion.

Such carbohydrate polymer substances include methylcellulose, carboxymethylcellulose, hydroxyalkylmethylcellulose, gum karaya, alginic acid and glycol esters of alginic acid, gum guar, psyllium, acacia and tragacanth as preferred agents to form the colloidal gel dispersions.

A preferred range in the amount of carbohydrate polymer substance utilized to prepare the colloid lubricating gel is not less than 0.5% by weight and not more than 7.5% by weight of the selected carbohydrate polymer substance or mixture of these. The selected carbohydrate polymer substance is dissolved in the same polar solvent as is used to prepare the solution of iodophor compound and iodine, and gentle heating at temperatures of not more than 50° C., may be employed to achieve complete dispersion.

The appropriate quantity of the iodine moiety, either as an iodophor compound or combined with the iodine carrier in solution, is then added to the formed colloidal dispersion of the carbohydrate polymer substance. The whole is then wet aside to gel, and packaged into appropriate unit-dose containers for use. When any of the iodophor carrier agents as are described above are used with iodine, the same order of mixing is preferred. While solutions are preferred, the dry powders may also be added to the carbohydrate polymer dispersion but greater care is required to avoid disturbing the balance than when solutions are used.

It may be desired to add appropriate pharmaceutical necessities to achieve special physiologically compatible needs for the product, as for example, pH buffers such as citric acid, sodium hydroxide and sodium acid phosphate, to provide a physiologically compatible pH range, and/or small quantities of a suitable surface-active agent to lower the surface tension of the formed gel and to increase its spreadability on the surface of catheters and instruments. Glycerin and other suitable glycols may be added to provide body to the gel as well as to enhance its humectant properties. When desired, perfumes and coloring aids may also be added.

The newly formed germicidal lubricating gels are homogenous, essentially transparent, brown gels with a viscosity of about 40,000 cps ±25%, when determined at 25° C., with a Brookfield Viscometer, fitted with a Helipath, T-Bar Spindle set at 2 to 5 rpm. The newly formed germicidal colloid lubricating gels are stable colloid preparations which retain the iodine content in an active form and are stable to aging for prolonged periods of time under elevated and ambient temperature conditions.

When the newly formed germicidal colloidal lubricating gel is brought into contact with micro-organisms, destruction of the microbial flora occurs almost instantaneously with a range in killing time observed for both gram-positive and gram-negative organisms to be as rapid as within 30 seconds to one minute. All microbial species are susceptible to the germicidally-active environment results, especially free of pathogens. Furthermore, it was found that a new preferential dynamic equilibrium is established between the available iodine and the iodine-carrying substance, (i.e., povidone and/or surfactant carrier such as nonylphenoxypoly-(ethylenoxy)-ethanol, and/or polaxamer copolymers, which are polyoxypropylenepoly(oxypropylene)-polyoxyethylene copolymers, and the carbohydrate polymer provides a new and unexpected property of self-sterilization of the colloid lubricating gel. In this manner, a packaged germicidal lubricating gel is sterile without being subjected to additional manufacturing steps wherein sterilization occurs. This is especially important since it is known that the usual sterilizing methods, as for example, heat, irradiation and/or chemical treatment results in a degradation of iodine-containing products and the chemical, physical and pharmaceutical properties of the composition does not permit filtration methods such as are used for sterilizing of pharmaceutical products.

When the new germicidal lubricating gels were tested for possible skin irritation, in accord with the methods of Draize, et al., as set forth in the "Appraisal of Chemicals in Foods, Drugs, and Cosmetics" published by the Association of Food and Drug Officials of the U.S., (1965), P.O. Box 1494, Topeka, Kans., or by the method of F. N. Marzulli, and D. L. Ruggles, reported in the Journal of the Association of Official Agricultural Chemists, 56: (1973) and, also as described in the Federal Hazardous Substances Act, 16 CFR, Chapter 11, (parts 1500.3, 1500.40, 1500.41, 1500.42), it was found that the lubricating gel was non-irritating to skin and mucous membranes and is not a primary skin irritant.

In practice, the formed germicidal lubricating colloid gel is applied to the surface of a catheter, as for example, a Foley Catheter of the Rusch-Gold Balloon Catheter, and other suitable catheters, as well as instruments, such as are used for insertion into the urethra and bladder, to provide lubricating-slip and a germicidal environment thereby enabling the easy insertion of the respective devices without tissue trauma or local injury. It will be found that when such instrumentation or catheterization takes place utilizing the new germicidal colloid lubricating gel to provide lubricating-slip, that the high incidence of urinary infection which is known to occur after such procedures in the past, will not be observed, thereby enhancing the diagnostic and therapeutic value of such procedures in lessening the patient rish of infection.

A microbiological study of the antimicrobial action of the new colloid lubricating gel on the micro-organisms present in the urethra of 20 subjects demonstrated that the new colloid lubricating gel has a profound degerming action and after one minute of contact time results in a 97.8% reduction of the mean microbial colony count present before the exposure to the new lubricating gel. In another study, the micro-organisms present in the urethra of normal individuals were markedly reduced when the new lubricating gel was installed for one minute to about 2% of the pre-treatment level and after 3 to 6 minutes of retention of the gel, only 0.7% of the original number of organisms remained. These studies demonstrate the excellent germicidal activity of the new gel composition and the resultant effect of minimizing the catheter conduit cause of post-treatment infection.

When a surfactant-iodophor forming compound is used in place of povidone-iodine, a non-surfactant iodophor compound, to form a new germicidal lubricating colloid gel, the same advantageous results are obtained as are described above. It is important that the ratio of the surfactant iodophor-former to carbohydrate polymer be within the range of from 0.3 parts to 4 parts by weight for each part of the carbohydrate polymer used and that the range of iodine in the colloid gel be within the range of 0.05% to not more than 25% of iodine content by weight of the gel.

DESCRIPTION OF PREFERRED EMBODIMENTS

The following Examples are given to further illustrate the present invention. The scope of the invention is not, however, meant to be limited to the specific details of the Examples.

EXAMPLE 1

In a suitable glass-reaction vessel fitted with a variable speed paddle agitator and a side-wall scraper is placed 150 ml. of distilled water and 6.9 gm. of hydroxypropylmethylcellulose is slowly added. The mixture is warmed, stirred, and when complete solution is achieved, the heat is removed but the temperature and stirring are maintained so that the solution is in a fluid state, and 60 gm. of propylene glycol is added.

In another vessel containing 100 ml. of distilled water is added 4.5 gm. of povidone-iodine and the mixture stirred until dissolved. When complete solution has been achieved, 1.5 gm. of glycerin is added. The povidone-iodine solution is then carefully mixed with the colloidal solution of hydroxypropylmethylcellulose.

Should it be desired to buffer the lubricating gel, then the well known compatible buffer salts such as citric acid and dibasic sodium phosphate may be used in sufficient amounts which are well known to the art. These buffer salts are added to the aqueous solution of povidone-iodine and prior to its addition to the hydroxypropylmethylcellulose solution. The preferred pH range for the new gel is between pH 4.5 and pH 5.5.

Should it be desired to include a surfactant agent to reduce the interfacial tension of the colloid gel, then any pharmaceutically acceptable surface active agent may be used in sufficient quantity to reduce the surface tension of the gel to below 35 dynes/cm$^2$ at 25° C. and generally requires from 0.05% to 0.25% by weight of the surface active agent to achieve this preferred surface tension.

The volume of the new composition is brought to 300 ml. with distilled water and the whole allowed to set at room temperature. The resultant brown, transparent, homogenous colloid gel contains 0.15% of available iodine and has a viscosity of about 40,000 cps with an accepted range of from not less than 30,000 cps and not more than 50,000 cps, when determined with the Brookfield RVT viscometer at 25° C. The formed gel is then packaged into unit containers to obtain germicidal lubrication of catheters and devices intended to be inserted into body cavities.

EXAMPLE 2

In a suitable reaction vessel fitted with a stirring device is placed 100 ml. of distilled water and 1 gm. of methylcellulose is added and the whole stirred until complete dispersion is achieved. When the dispersion is uniform, then 2 gm. of povidone are added and the mixture stirred until complete solution is achieved. To this composition is added 0.2 gm. of finely-divided iodine crystals, in small increments, with stirring to avoid elevated temperature. Successive increments of iodine are added after the preceding portion has been dissolved. The colloid dispersion is stirred for at least one hour, or until it is determined that a carbon tetrachloride extract of a sample of the composition does not give a positive iodine test and the vapor pressure determined for the respective sample of the preparation is essentially zero.

To this composition is now added 20 gm. of propylene glycol and 0.1 gm. of glycerin. A small quantity of about 0.1% by weight of a suitable non-ionic surface active agent, such as nonylphenoxypoly (ethylenecoxy) ethanol, which is known in the trade as Igepal, a compound marketed by the GAF Corporation, Chemical Division of New York, N.Y. which amount is sufficient to lower the surface tension of the composition to 28 dynes/cm$^2$. The volume of the composition is now brought to 200 ml. with a solution containing 0.07% of sodium dibasic phosphate and 0.035% of citric acid. Two drops of 5% sodium hydroxide solution are added to adjust the pH of the composition of pH 5.

The resultant composition is a brown, transparent, homogenous colloid gel with a viscosity of 38,000 cps containing 0.2% of available iodine in stable homogenous colloid dispersion. The formed gel is packaged into unit containers, each containing 10 gm. of the newly formed germicidal colloidal lubricating gel, which is now ready for use to lubricate catheters and instruments.

EXAMPLE 3

When it is desired to use alginic acid as the colloid gelling agent to prepare the microbicidal lubricating gel, then from 2% to 5% of alginic acid is utilized. A preferred form of alginic acid is sodium alginate and a small quantity of calcium ions is added to stabilize the gel-forming properties of sodium alginate solutions so that a solid, firm gel results. Such calcium salts as calcium gluconate, calcium tartrate, calcium citrate, calcium salicylate or any other salt capable of yield calcium ions may be used. Magnesium ions also may be used to enhance the gelling properties of sodium alginate and such magnesium salts as are capable of yielding magnesium ions may be utilized for this purpose. Optimal magnesium salts for this purpose are the double salt magnesium and choline salicylate, magnesium salicylate, magnesium sulfate and magnesium chloride.

To prepare the new germicidal lubricating colloid gel with sodium alginate, approximately 0.1 gm. of calcium gluconate is dissolved in about 100 gm. of water, and to this is added 2 gm. of sodium alginate, and 0.5 gm. of propylene glycol. The mixture is stirred until a uniform disperson results, then 1 gm. povidoneiodine USP is added. The mixture is brought to volume of 200 ml. with water and the whole set aside until the gelling stage has been completed. The resultant gel is amber-colored and transparent, with a viscosity of 32,000 cps and contains 0.1% available iodine. The new gel is stable for prolonged periods of time and possesses desirable antimicrobial properties against all classes of microorganisms.

A particular advantage of the new alginic and colloid gel base is that it may be buffered to be within the acid range in contrast to conventional sodium alginate ointment bases, which are not stable below pH 4.5 and most often are formulated to be above pH 6, a pH range incompatible with iodine.

An alternate compound to alginic acid as a gelling agent is the propylene glycol ester of alginic acid and the glycerin ester of aglinic acid, both of which compounds are used in a sufficient quantity to yield a concentration of alginic acid of from 3% to 5% by weight of the finished product. When the propylene glycol ester of alginic acid or the calcium ester of alginic acid is used, it is not necessary to add propylene glycol or glycerin as a bodying agent. The remainder of the steps are the same and the resulting product possesses the same properties as described for the products obtained as a result of Examples 1 and 2 above.

EXAMPLE 4

In place of the hydroxypropylmethylcellulose and the carboxymethylcellulose described in Examples 1 through 3 above, there may be added suitable cellulose derivatives, as for example, hydroxymethylcellulose, hydroxyethylcellulose, hydroxypropylcellulose and carboxymethylcellulose which name is also used for its sodium salt, sodiumcarboxymethylcellulose. The range in concentration of the respective cellulose derivative selected is not less than 0.5% and not more than 7.5% by weight of the toral weight of the composition being prepared. Mixtures of the cellulose derivatives may be used but the total concentration range as described above remains the same.

The formed germicidal lubricating colloid gels prepared with the respective cellulose derivatives possess the same physiologic and germicidal properties described above and the essential differences amoung the respective formed gels in the resultant viscosity of the finished gel. Thus, it may be desirable to use a cellulose derivative forming a more viscous colloid gel in southern geographic regions wherein the temperature is necessarily higher than that of the northern regions. Care should be taken when the upper limit of concentration of the cellulose substance is used in a particular product formulation in that the temperature during manufacture is not elevated about room temperature, since heat will tend to coagulate the more concentrated, viscous colloid gel dispersions in the presence of iodine.

When the germicidal lubricating gels prepared as described above were stood for prolonged periods, there were no stratification or separation into layers and also, the integrity of the available iodine content was maintained, thus insuring the germicidal antimicrobial activity of the preparation. Furthermore, the iodine content was complexed in a form that it could not be extracted by carbon tetrachloride and the vapor pressure of the product was essentially zero to establish the combined complexed state of the new compositions.

EXAMPLE 5

In place of the pevidone-iodine used in Examples 1, 3 and 4 above, there may be added a surfactant iodophor compound such as nonylphenoxypoly-(ethyleneoxy) ethanol iodine complex, or polyoxypropylene poly-(oxypropylene)-polyoxyethylene copolymers, which are known by the generic name, iolyxamers, and which are marketed by Wyandotte Chemical Corporation of Midlands, Mich., in the range of concentration from 0.3 parts by weight to 4 parts by weight of the surfactant iodopher compound for each part of carbohydrate polymer used to prepare the gel. The critical determirant for the overall ratio of the amount of surfactant iodopher compound used is the concentration of iodine complexed to the respective carrier moiety. The concentration of iodine in these iodopher preparations may be as high as 40% and as low as 0.1% by weight.

When the surfactant iodophor compounds are used to prepare the new germicidal lubricating colloid gel, then the use of a surface active agent to enhance the spreading qualities of the formed lubricating gel is not necessary since the surface tension of the formed composition will be below 30 dynes/cm$^2$. The order of mixing of the respective compounds remains the same as described above. The resultant formed lubricating gels have a viscosity of between 30,000 cps and 50,000 cps and are stable for prolonged storage periods, retaining their advantageous broad spectrum antimicrobial properties.

EXAMPLE 6

In place of the alginic acid, and/or the propylene glycol esters of alginic acid, and/or the glycerin ester of alginic acid as the gelling agent described in Example 3, there may be substituted an equivalent part by weight or tragacanth and/or gum karaya as colloidal gelling agents. However, when such substances are used as gelling agents it may be found desirable to add a gelling accelerator of from 0.1 part to 0.3 parts by weight of such cellulose-gelling agents as described in Examples 1, 2 and 4 above. The remainder of the manufacturing steps are the same, and the resulting germicidal lubricating colloid gels possess the same advantageous properties as the preparations described above.

EXAMPLE 7

When it is desired to utilize the new formed germicidal lubricating colloid gel to facilitate the insertion of a catheter and/or instrument into the urethra, then the following procedure is utilized.

(a) The patient is surgically prepared and the anogenital area is aseptically cleansed with a germicidal soap; the surrounding skin areas cleansed with a suitable topical germicide and the area draped.

(b) The sterile device is then coated with the newly formed germicidal lubricating colloid gel and carefully introduced into the urethra into the bladder. Since trauma contributes to the development of infection, the appropriate catheter size should be used and the catheter and/or instrument should not be forced if any resistance is encountered. The balloon catheter is the preferred retention catheter with the balloon inflated to hold the catheter in the bladder.

(c) After the insertion of the retention catheter, an antiseptic germicidal ointment is placed around the catheter to help minimize infection by the catheter conduit route.

(d) A closed sterile drainage system is imperative and urine cultures with colony counts should be obtained periodically. The urine container should be lower than the catheter and the drainage system supplied with a valve to prevent the reflux flow of urine. At least, a daily change of container is imperative and this should be done more often if contamination is evident. It is important that the prophylactic use of systemic antibiotics be avoided, unless these are specially required, since relatively innocuous organisms have shown to be replaced by virulent pathogens. Indwelling catheters must be changed at least every 7 to 10 days.

When the above procedure is conducted with the newly formed germicidal lubricating colloid gel, the incidence of posttreatment infection is virtually eliminated, and the procedure is essentially without tissue trauma in contrast to the known injuries experiences reported after similar procedures, using older lubricating gels.

While the invention has been illustrated with respect to particular compositions, it is apparent that variations and modifications can be made.

What is claimed is:

1. An aqueous germicidal colloidal lubricating gel, comprising water, 0.05–2% by weight iodine, 0.5–7.5% by weight of a physiologically compatible gel-forming colloid selected from the group consisting of methylcellulose, carboxymethylcellulose, hydroxyalkylcellulose, gum karaya, alginic acid, glycol esters of alginic acid, gum guar, pslyllium, acacia and tragacanth, an iodophor-former selected from the group consisting of 0.5–2 parts by weight per part of said colloid of polyvinylpyrrolidone and 0.3–4 parts by weight per part of said colloid of nonylphenoxypoly-(ethyleneoxy)-ethanol and polyoxypropylenepoly-(oxy-propylene) polyoxyethylene copolymers.

2. Composition according to claim 1 wherein said iodophor-former is polyvinylpyrrolidone and is present in an amount of 0.5–2 parts by weight per each part of said colloid.

3. Composition according to claim 1 wherein said iodophor-former is a surfactant and is present in an amount of 0.3–4 parts by weight per each part of said colloid.

4. Method of inserting a medical instrument into a body cavity without substantial irritation or pain and with reduced risk of infection and tissue trauma, which comprises lubricating the instrument with the aqueous germicidal colloidal lubricating gel of claim 1, and inserting the thus lubricated instrument into the selected body cavity.

* * * * *